United States Patent
Shen

(10) Patent No.: US 7,369,693 B2
(45) Date of Patent: May 6, 2008

(54) THORACIC CAGE COORDINATE SYSTEM FOR RECORDING PATHOLOGIES IN LUNG CT VOLUME DATA

(75) Inventor: Hong Shen, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 665 days.

(21) Appl. No.: 10/870,305

(22) Filed: Jun. 17, 2004

(65) Prior Publication Data

US 2005/0010107 A1    Jan. 13, 2005

Related U.S. Application Data

(60) Provisional application No. 60/480,653, filed on Jun. 23, 2003.

(51) Int. Cl.
*G06K 9/00* (2006.01)
(52) U.S. Cl. ..................... 382/128; 382/293
(58) Field of Classification Search ............ 382/131, 382/128, 293; 378/4, 21, 23, 25; 250/363.04, 250/362.02; 345/645
See application file for complete search history.

(56) References Cited

U.S. PATENT DOCUMENTS

| | | | |
|---|---|---|---|
| 5,807,256 A | * | 9/1998 | Taguchi et al. ............ 600/425 |
| 6,160,398 A | * | 12/2000 | Walsh ....................... 324/309 |
| 6,345,113 B1 | * | 2/2002 | Crawford et al. ............ 382/131 |
| 6,577,752 B2 | * | 6/2003 | Armato et al. ............... 382/131 |
| 6,594,378 B1 | * | 7/2003 | Li et al. ...................... 382/128 |
| 6,690,762 B1 | * | 2/2004 | Berestov ...................... 378/62 |

OTHER PUBLICATIONS

Dansereau et al., Measurements of the Three-Dimensional Shape of the Rib Cage, 1988, J. Biomechanics Pergamon Press plc, vol. 21, No. 11, pp. 893-901.*

* cited by examiner

*Primary Examiner*—Matthew C. Bella
*Assistant Examiner*—Dennis Rosario
(74) *Attorney, Agent, or Firm*—Donald B. Paschburg; F. Chau & Associates, LLC

(57) ABSTRACT

We introduce a thoracic cage coordinate system for recording pathology locations in lung CT volume data. The centerlines of each individual rib are extracted and labeled from top to bottom. For each pair of ribs, a three-dimensional ("3D") orthogonal basis is computed by eigen-analysis of the rib centerline points, which are taken as the x, y, and z axes. The rib pairs form a set of reference planes. Therefore, there are a set of coordinate systems (x, y, z), each of which is locally valid between two adjacent planes. To define a location globally, a fourth parameter, n, is added to identify the serial number of the reference plane. The complete coordinate is recorded as (n, x, y, z). This system is robust against deformations due to bending and twisting, and is relatively stable over inhalation. Further, this system may be readily adapted in other 3D modalities, such as MRI volume data.

16 Claims, 4 Drawing Sheets

THORACIC CAGE COORDINATE SYSTEM FOR RECORDING PATHOLOGIES IN LUNG CT VOLUME DATA

CROSS-REFERENCE TO RELATED APPLICATIONS

This application claims priority to U.S. Provisional Application No. 60/480,653, which was filed on Jun. 23, 2003, and which is fully incorporated herein by reference.

BACKGROUND OF THE INVENTION

1. Field of the Invention

The present invention relates to the field of computer tomography (CT), and, more particularly, to a thoracic cage coordinate system for denoting pathology locations in lung CT volume data.

2. Description of the Related Art

With the development of multi-slice computer tomography ("CT") scanners, computer-aided diagnosis ("CAD") algorithms and software can provide functionalities that make reading CT volume data more convenient and effective. An important task of CAD software is to record pathology locations as a basic reporting functionality. For example, the locations of lung nodules, which indicate possible lung cancer, may be recorded after they are found by physicians or by a CAD module.

Currently available recording schemes are generally not satisfactory. Internally, they record pathology locations using a patient coordinate system (i.e., x, y and z coordinates). When displayed for physicians, such pathology locations are coarsely referenced even with respect to simple lung anatomic structures, such as lung lobes. Because the patient coordinate system depends largely on patient pose and translations, it is generally inaccurate.

Thus, it would be advantageous to provide a coordinate system that is independent of patient pose and translations. Further, the coordinate system should be stable over small deformations of the patient's body or inhalation level.

SUMMARY OF THE INVENTION

In one aspect of the present invention, a computer-implemented method of creating and using a thoracic cage coordinate system from a thoracic cage is provided. The thoracic cage comprises a plurality of individual rib centerlines. The method includes grouping pairs of individual rib centerlines into a plurality of rib centerline pairs; constructing a local coordinate system for each of the plurality of rib centerline pairs; constructing a global coordinate system using the local coordinate systems of the plurality of rib centerline pairs; and determining thoracic cage coordinates of a pathological location in the global coordinate system, wherein the pathological location is defined by a patient coordinate system.

In another aspect of the present invention, a machine-readable medium having instructions stored thereon for execution by a processor to perform method of creating and using a thoracic cage coordinate system from a thoracic cage is provided. The thoracic cage comprises a plurality of individual rib centerlines. The method includes grouping pairs of individual rib centerlines into a plurality of rib centerline pairs; constructing a local coordinate system for each of the plurality of rib centerline pairs; constructing a global coordinate system using the local coordinate systems of the plurality of rib centerline pairs; and determining thoracic cage coordinates of a pathological location in the global coordinate system, wherein the pathological location is defined by a patient coordinate system.

In yet another aspect of the present invention, a system of creating and using a thoracic cage coordinate system from a thoracic cage is provided. The thoracic cage comprises a plurality of individual rib centerlines. The system includes means for grouping pairs of individual rib centerlines into a plurality of rib centerline pairs; means for constructing a local coordinate system for each of the plurality of rib centerline pairs; means for constructing a global coordinate system using the local coordinate systems of the plurality of rib centerline pairs; and means for determining thoracic cage coordinates of a pathological location in the global coordinate system, wherein the pathological location is defined by a patient coordinate system.

BRIEF DESCRIPTION OF THE DRAWINGS

The invention may be understood by reference to the following description taken in conjunction with the accompanying drawings, in which like reference numerals identify like elements, and in which.

DETAILED DESCRIPTION OF PREFERRED EMBODIMENTS

Figure 1:
FIG. 1 depicts an axial slice image from an exemplary chest CT volume data, in accordance with one embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

We introduce a thoracic cage coordinate system for recording pathology locations in lung computer tomography ("CT") volume data. The thoracic cage is composed of pairs of ribs, the spine and the sternum. These features, especially the rib pairs, have at least the following advantages. First, they are very stable and prominent in CT data, and hence, can be reliably extracted even from noisy data sets. Second, they cover the complete lung area and part of the lower abdomen, which make them suitable for lung applications. Third, the rib structures are highly ordered and symmetrical, and each pair of ribs roughly forms a plane. Fourth, they are relatively less affected by lung surgery.

The centerlines of each individual rib are extracted and labeled from top to bottom. For each pair of ribs, a three-dimensional ("3D") orthogonal basis is computed by eigen-analysis of the rib centerline points, which are taken as the x, y, and z axes. The rib pairs form a set of reference planes. Therefore, there are a set of coordinate systems (x, y, z), each of which is locally valid between two adjacent planes. To define a location globally, a fourth parameter, n, is added to identify a serial number of each reference plane. The complete coordinate is recorded as (n, x, y, z). This system is robust against deformations due to bending and twisting, and is relatively stable over inhalation. Further, this system may be readily adapted in other 3D modalities, such as magnetic resonance imaging ("MRI") volume data.

Referring now to FIG. 1, an axial slice image from an exemplary chest CT volume data 100 is shown, in accordance with one embodiment of the present invention. The elliptical and high-intensity regions 105 are the rib cross-sections in this slice. We extract the centerlines of each individual rib using a tracing-based approach. That is, we detect the seed points at the center of each rib, and trace along the rib centerlines. We extract these centerlines, and perform post-processing on them. In the post-processing procedure, we smooth the centerlines, label them from top to bottom, and from left to right. We pair the corresponding left and right rib centerlines.

A. The Local Coordinate System

Figure 2:
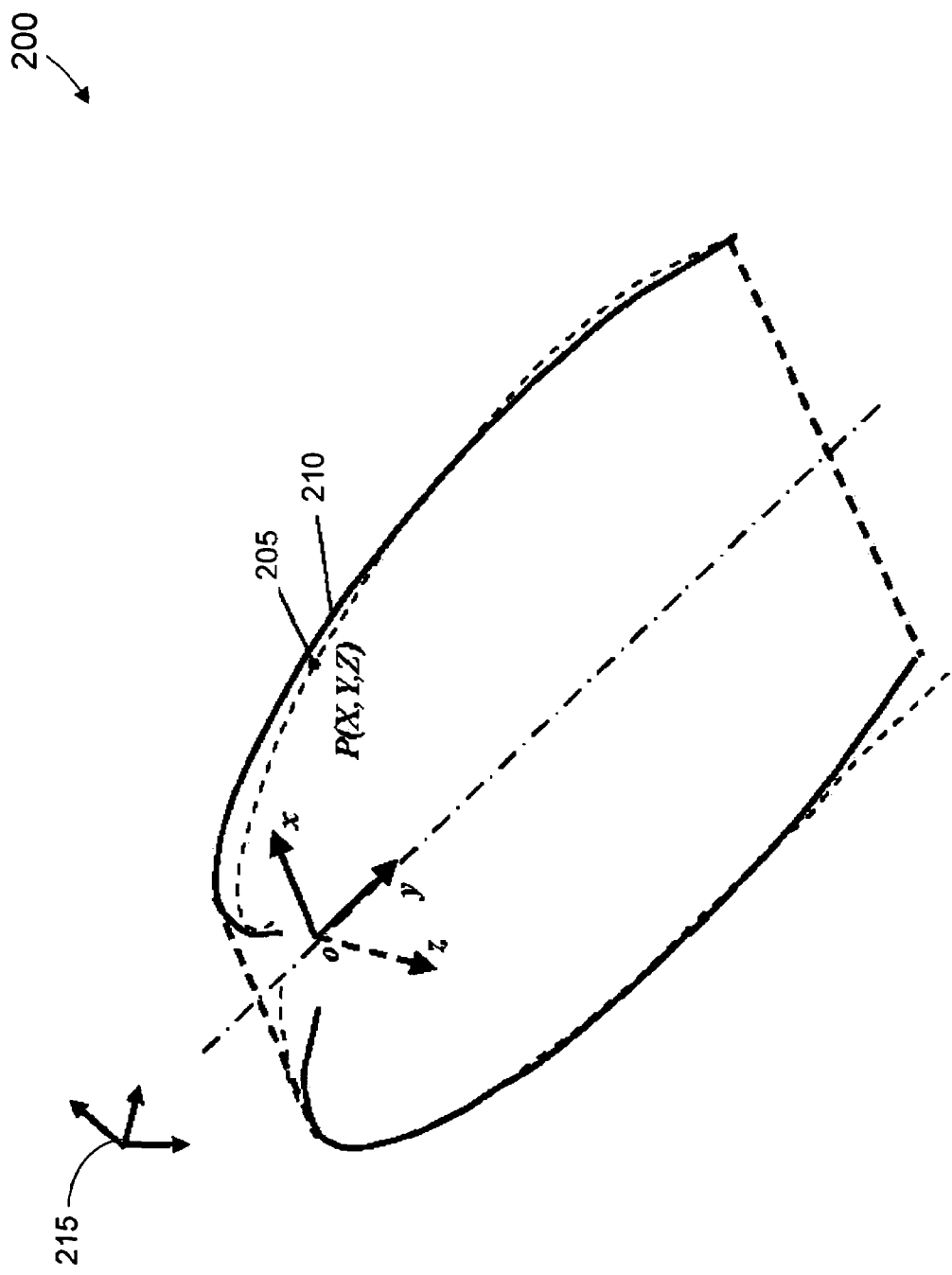
FIG. 2 depicts a local coordinate system formed by a pair of rib centerlines, in accordance with one embodiment of the present invention.

Referring now to FIG. 2, a local coordinate system 200 formed by a pair of rib centerlines is shown, in accordance with one embodiment of the present invention. The dotted lines 205 are rib centerline points, and the solid lines 210 are a projection of the rib centerline points onto a plane.

For each pair of ribs, a covariance matrix is computed from the x, y and z locations of all centerline points. We perform eigen-analysis on each pair of ribs to obtain a 3D orthogonal basis. As previously mentioned, the centerline points of a pair of ribs roughly fall on a plane, which makes an angle with an axial plane of slice images.

Among the three elgenvalues, the smallest one is much smaller than the other two. Among the three eigenvectors, the eigenvector associated with the smallest eigenvalue is the normal of the plane that is roughly formed by the centerline points of this rib pair. We take this engenvector as the z-axis of the coordinate system. Due to the symmetry of the pair of ribs, one of the other two eigenvectors will be the symmetrical axis of the two ribs, which is taken as the y-axis of the coordinate system. The other eigenvector is taken as the x-axis. To define the origin of the coordinate system, we find the intersection of the spinal cord with the x-y plane, the plane formed by the x and y axes defined above, and use the center of the intersection as the origin. As shown in FIG. 2, o is the center of the intersection of the spinal cord as the origin, and x, y, z represents the three axes 220 of the new coordinate system. The three axes 215 in the upper-left corner represent the original patient coordinate system. Obviously, the z axis of the new coordinate system makes an angle with the original axial direction. Due to the distortions of the lung tissues from body twists, the above coordinate system may be only approximately valid. The farther away a point is from the rib pairs that define the coordinate system, the less accurate the coordinates are. Therefore, we call this coordinate system a local system, which should be used primarily for points between two adjacent planes.

B. The Global Coordinate System

The planes formed by different rib pairs are usually not parallel. Their normal may vary gradually, and independent of each other. To form a globally valid coordinate system, we need a fourth descriptor to record which pair of adjacent planes is the pathology located in between. This number, denoted herein by n, may be an integer, ranging from 0 to 8, because there are usually nine (9) rib pairs covered by a chest CT scan. A value of n means that the pathology is location between rib plane n and n+1, and we use the nth plane as its "reference plane." The plane numbers counts from top to bottom.

Figure 3:
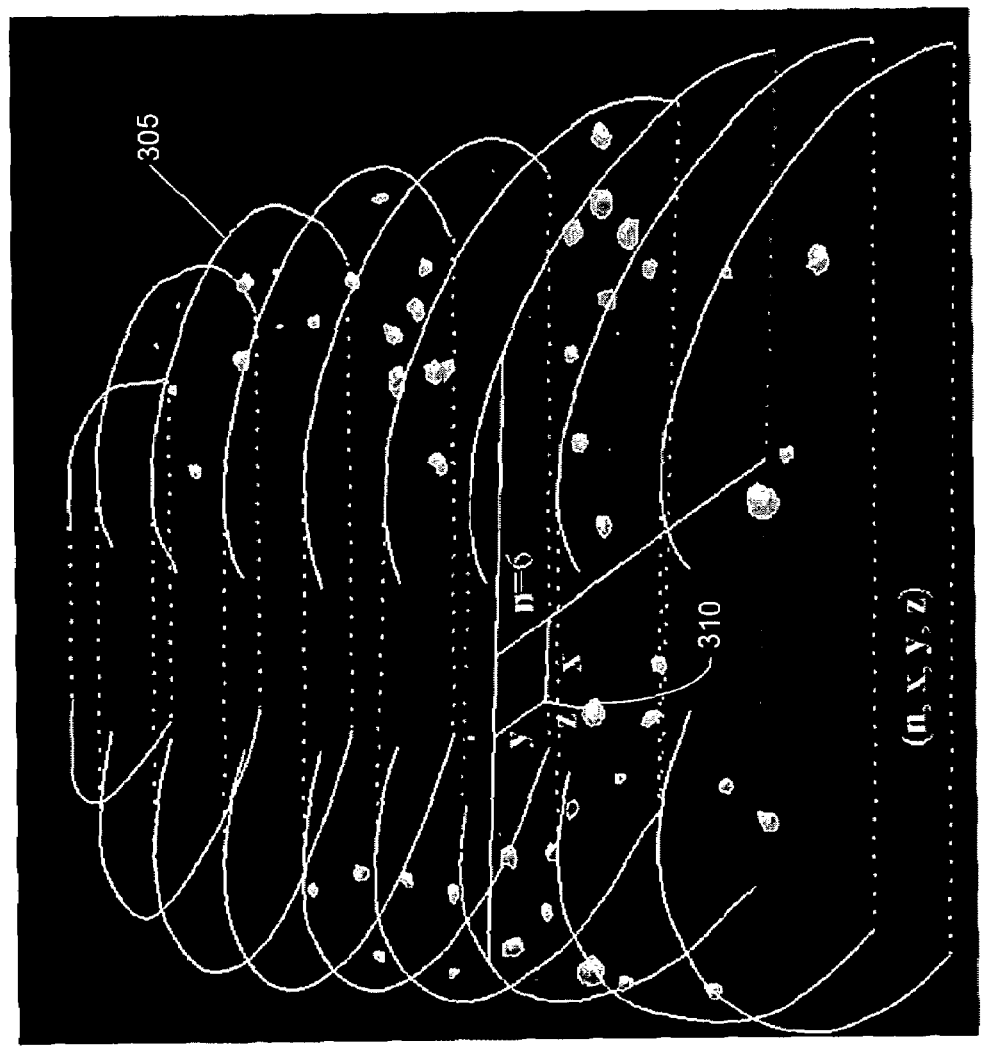
FIG. 3 depicts a thoracic cage coordinate system, in accordance with one embodiment of the present invention.

Referring now to FIG. 3, a thoracic cage coordinate system 300 is shown, in accordance with one embodiment of the present invention. The curves 305 are not the rib centerline points. Rather, the curves 305 are the projected centerline points (shown as 210 on FIG. 2) on the planes formed by the rib pairs. We use them here as visual boundaries of the planes. Displayed in this system are the lung nodules. Their locations can be uniquely recorded by the four coordinates: n, x, y, and z. For example, the marked nodule 310 in FIG. 3 has n=6, which means it is located between the sixth and seventh plane. We use the sixth plane as the reference plane. The z coordinate is actually the distance to the reference plane. If we project the nodule onto the reference plane, the y coordinate is the distance between the projected location to the symmetric axis of the projected ribs centerline points. The x coordinate is the distance between the projected location to the spinal cord center in the direction of the symmetric axis.

Figure 4:
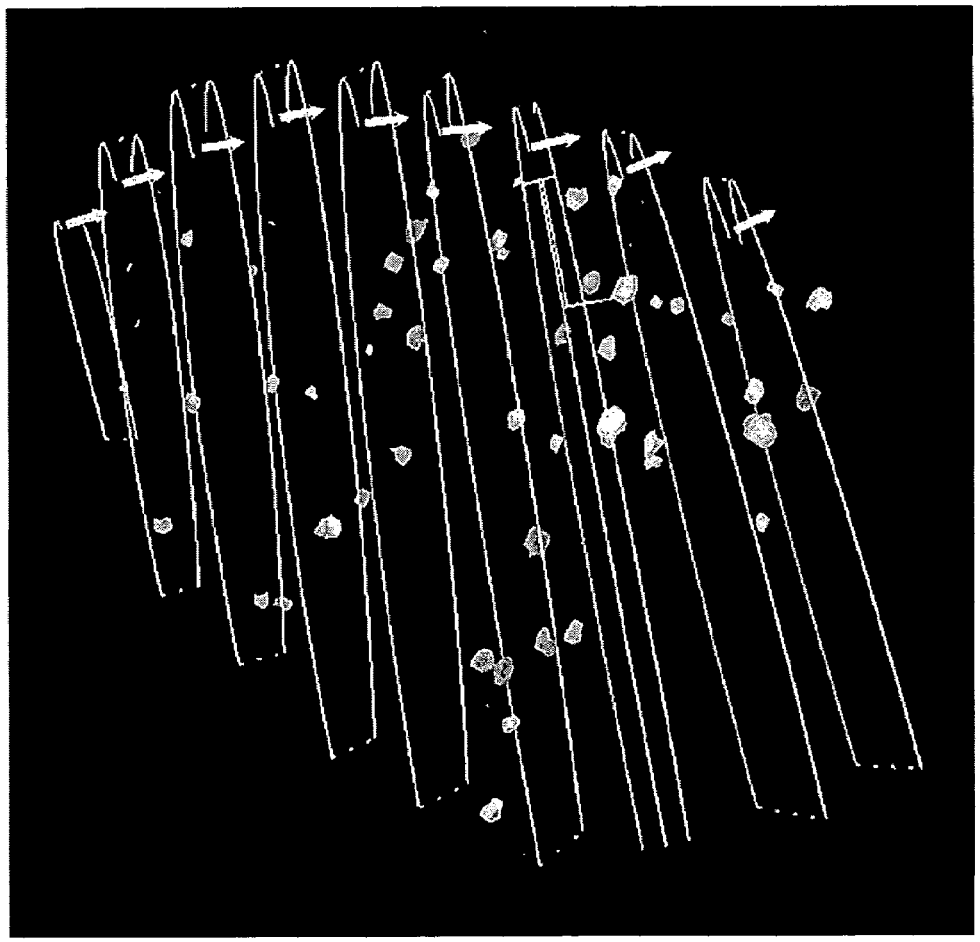
FIG. 4 depicts a side view of the rib centerline planes, in accordance with one embodiment of the present invention.

Referring now to FIG. 4, a side view 400 of the rib centerline projections (i.e., the curves 305) of FIG. 3 is shown, in accordance with one embodiment of the present invention. The projected centerline curves form parts of the plane boundaries. The arrows show the normal or z-axes of the planes. The dull ends of the arrows mark the spine cord centers on these planes. It is clear that the normal of the rib planes vary gradually from top to bottom. These directions are relatively independent of each other, and from the bending of the human body.

C. Using the Global Coordinate System

The rib centerline coordinate system is mathematically defined by a set of transformation matrices $$T^{(k)}_{XYZ \to xyz}, k=1 \ldots n \tag{1}$$

where n is the total number of rib pairs.

To convert a location (X, Y, Z) in the original patient coordinate system into (n, x, y, z) in the global rib centerline coordinate system, we compute their coordinates in all the location coordinate systems:

$$(x_k\ Y_k\ Z_k\ 1) = T^{(k)}_{XYZ \to xyz}(X\ Y\ Z\ 1) \tag{2}$$

where k=1. . . n. We compare the z-coordinate value $z_k$, k=1. . . n, to find k such that $$z_k \geq 0 \text{ and } z_{k+1} < 0 \tag{3}$$

This means that the location is between the $k^{th}$ and $k+1^{th}$ rib planes, and hence assigned to the $k^{th}$ local coordinate system. Therefore, $$(n\ x\ y\ z) = (k\ x_k\ y_k\ z_k) \quad (4)$$

We have defined a thoracic cage coordinate system to denote pathology locations in lung CT volume data. Since we use one set of orthogonal basis between each pair of rib planes, and augment them with the plane number, the coordinate values will still be valid when the spine is deformed due to body bending and twisting. Also, this system is independent of pose and translations.

Among a variety of other potential applications, the rib centerline coordinate system can be used in area of computer-aided diagnosis in various medical imaging modalities.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A computer-implemented method of creating and using a thoracic cage coordinate system from a thoracic cage, the thoracic cage comprising a plurality of individual rib centerlines, comprising:
   grouping pairs of individual rib centerlines into a plurality of rib centerline pairs;
   constructing a local coordinate system for each of the plurality of rib centerline pairs;
   constructing a global coordinate system using the local coordinate systems of the plurality of rib centerline pairs; and
   determining thoracic cage coordinates of a pathological location in the global coordinate system, wherein the pathological location is defined by a patient coordinate system, wherein constructing a local coordinate system for each of the plurality of rib centerline pairs comprises:
   computing a covariance matrix on the locations of all points on each of the plurality of rib centerline pairs;
   performing eigen-analysis on each of the covariance matrices to obtain three eigenvalues and three eigenvectors for each of the plurality of covariance matrices;
   forming a three-dimensional ("3D") orthogonal basis from the three eigenvectors for each of the covariance matrices; and
   defining an origin on a spinal cord.

2. The computer-implemented method of claim 1, wherein forming a three-dimensional ("3D") orthogonal basis from the three eigenvectors comprises:
   assigning one of the three eigenvectors that corresponds to the smallest of the three eigenvalues as a z-axis of the local coordinate system;
   assigning one of the three eigenvectors that corresponds to the middle of the three eigenvalues as a y-axis of the local coordinate system;
   assigning one of the three eigenvectors that corresponds to the highest of the three eigenvalues as a x-axis of the local coordinate system; and
   forming a transformation matrix using the three eigenvectors for each of the covariance matrices.

3. The computer-implemented method of claim 1, wherein defining an origin on a spinal cord comprises:
   determining a plane whose normal is a z-axis for each of the plurality of local coordinate systems;
   obtaining a cross-section of the spinal cord with each of the plurality of planes; and
   assigning the cross-section as the origin of the each of the plurality planes.

4. The computer-implemented method of claim 1, wherein constructing a global coordinate system using the local coordinate systems comprises:
   labeling each of the plurality of rib centerline pairs, wherein the global coordinate system comprises all of labeled rib centerline pairs.

5. The-computer-implemented method of claim 4, wherein labeling each of the plurality of rib centerline pairs comprises labeling each of the plurality of rib centerline pairs from top to bottom.

6. The computer-implemented method of claim 4, wherein labeling each of the plurality of rib centerline pairs comprises labeling each of the plurality of rib centerline pairs from left to right.

7. The computer-implemented method of claim 4, wherein labeling each of the plurality of rib centerline pairs comprises labeling each of the plurality of rib centerline pairs in a sequential numerical order.

8. A computer-implemented method of creating and using a thoracic cage coordinate system from a thoracic cage, the thoracic cage comprising a plurality of individual rib centerlines, comprising:
   grouping pairs of individual rib centerlines into a plurality of rib centerline pairs;
   constructing a local coordinate system for each of the plurality of rib centerline pairs;
   constructing a global coordinate system using the local coordinate systems of the plurality of rib centerline pairs; and
   determining thoracic cage coordinates of a pathological location in the global coordinate system, wherein the pathological location is defined by a patient coordinate system, wherein determining thoracic cage coordinates of a pathological location in the global coordinate system comprises:
   transforming the pathological location into each of the local coordinate systems using a transformation matrix of each of the local coordinate systems;
   recording the thoracic cage coordinates in each of the local coordinate systems; and
   determining which of the local coordinate systems to use by comparing z-coordinates of the thoracic cage coordinates.

9. A machine-readable medium having instructions stored thereon for execution by a processor to perform method of creating and using a thoracic cage coordinate system from a thoracic cage, the thoracic cage comprising a plurality of individual rib centerlines, comprising:
   grouping pairs of individual rib centerlines into a plurality of rib centerline pairs;
   constructing a local coordinate system for each of the plurality of rib centerline pairs;
   constructing a global coordinate system using the local coordinate systems of the plurality of rib centerline pairs; and
   determining thoracic cage coordinates of a pathological location in the global coordinate system, wherein the pathological location is defined by a patient coordinate system, wherein constructing a local coordinate system for each of the plurality of rib centerline pairs comprises:
computing a covariance matrix on the locations of all points on each of the plurality of rib centerline pairs;
performing eigen-analysis on each of the covariance matrices to obtain three eigenvalues and three eigenvectors for each of the plurality of covariance matrices;
forming a three-dimensional ("3D") orthogonal basis from the three eigenvectors for each of the covariance matrices; and
defining an origin on a spinal cord.

10. The machine readable medium of claim 9, wherein forming a three-dimensional ("3D") orthogonal basis from the three eigenvectors comprises:
assigning one of the three eigenvectors that corresponds to the smallest of the three eigenvalues as a z-axis of the local coordinate system;
assigning one of the three eigenvectors that corresponds to the middle of the three eigenvalues as a y-axis of the local coordinate system; assigning one of the three eigenvectors that corresponds to the highest of the three eigenvalues as a x-axis of the local coordinate system; and
forming a transformation matrix using the three eigenvectors for each of the covariance matrices.

11. The machine readable medium of claim 9, wherein defining an origin on a spinal cord comprises:
determining a plane whose normal is a z-axis for each of the plurality of local coordinate systems;
obtaining a cross-section of the spinal cord with each of the plurality of planes; and
assigning the cross section as the origin of the each of the plurality planes.

12. The machine readable medium of claim 9, wherein constructing a global coordinate system using the local coordinate systems comprises:
labeling each of the plurality of rib centerline pairs, wherein the global coordinate system comprises all of the labeled rib centerline pain.

13. The machine readable medium of claim 12, wherein labeling each of the plurality of rib centerline pairs comprises labeling each or the plurality of rib centerline pairs from top to bottom.

14. The machine readable medium of claim 12, wherein labeling each of the plurality of rib centerline pairs comprises labeling each of the plurality of rib centerline pairs from left to right.

15. The machine readable medium of claim 12, wherein labeling each of the plurality of rib centerline pairs comprises labeling each of the plurality of rib centerline pairs in a sequential numerical order.

16. A machine-readable medium having instructions stored thereon for execution by a processor to perform method of creating and using a thoracic cage coordinate system from a thoracic cage the thoracic cage comprising a plurality of individual rib centerlines, comprising:
grouping pairs of individual rib centerlines into a plurality of rib centerline pairs;
constructing a local coordinate system for each of the plurality of rib centerline pairs;
constructing a global coordinate system using the local coordinate systems of the plurality of rib centerline pairs: and
determining thoracic cage coordinates of a pathological location in the global coordinate system, wherein the pathological location is defined by a patient coordinate system, wherein determining thoracic cage coordinates of a pathological location in the global coordinate system comprises:
transforming the pathological location into each of the local coordinate systems using a transformation matrix of each of the local coordinate systems;
recording the thoracic cage coordinates in each of the local coordinate systems; and
determining which of the local coordinate systems to use by comparing z-coordinates of the thoracic cage coordinates.

* * * * *